US012799150B2

(12) United States Patent
Mukherjee et al.

(10) Patent No.: US 12,799,150 B2
(45) Date of Patent: Nov. 17, 2026

(54) PROCESS FOR THE PREPARATION OF N4-HYDROXYCYTIDINE AND ITS DERIVATIVES

(71) Applicant: COUNCIL OF SCIENTIFIC AND INDUSTRIAL RESEARCH, New Delhi (IN)

(72) Inventors: Debaraj Mukherjee, Jammu (IN); Qazi Naveed Ahmed, Jammu (IN); Ajaz Ahmed, Jammu (IN); Junaid Shafi Banday, Jammu (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 359 days.

(21) Appl. No.: 18/558,928

(22) PCT Filed: May 6, 2022

(86) PCT No.: PCT/IN2022/050442

§ 371 (c)(1),
(2) Date: Nov. 3, 2023

(87) PCT Pub. No.: WO2022/234598

PCT Pub. Date: Nov. 10, 2022

(65) Prior Publication Data

US 2024/0239832 A1 Jul. 18, 2024

(30) Foreign Application Priority Data

May 6, 2021 (IN) ............................ 202111020678

(51) Int. Cl.
*C07H 19/067* (2006.01)

(52) U.S. Cl.
CPC .................................. *C07H 19/067* (2013.01)

(58) Field of Classification Search
CPC ................................ C07H 19/067; C07H 1/00
See application file for complete search history.

(56) References Cited

U.S. PATENT DOCUMENTS

2014/0235566 A1 8/2014 Amblard et al.

FOREIGN PATENT DOCUMENTS

WO 2016106050 A1 6/2016
WO 2019113462 A1 6/2019

OTHER PUBLICATIONS

Beutner, Org. Process Res. Dev. 2019, 23, 2050-2056. (Year: 2019).*

Beutner, Org. Process Res. Dev. 2019, 23, Supplementary information. (Year: 2015).*

Yew, Wing Wai, et al. "Oxidative Stress and First-Line Antituberculosis Drug-Induced Hepatotoxicity." Antimicrobial Agents and Chemotherapy. Aug. 2018, vol. 62, Issue 8. pp. 1-10.

Articles of Significant Interest Selected from This Issue by the Editors. Journal of Virology. Feb. 2018, vol. 92, Issue 3. pp. 1-2 https://doi.org/10.1128/JMI02026-17.

Gopalsamuthiram, Vijayagopal et al. "A Concise Route to MK-4482 (EIDD-2801) from Cytidine: Part 2" ChemRxiv. Preprint. 3 pages. doi:10.26434/chemrixiv.12931445.v1.

Ahlqvist, Grace et al. "Progress Toward a Large-Scale Synthesis of Molnupiravir (MK-4482, EIDD-2801) from Cytidine." ACS Omega 2021, 6, pp. 10396-10402, Published: Apr. 8, 2021 doi:10.1021/acsomega.1c00772.

Vasudevan, N. et al. "A concise route to MK-4482 (EIDD-2801) from cytidine." Chem. Connun, 2020, 56, 13363-13364. doi:10.1039/d0cc05944g.

International Search Report and Written Opinion issued Jul. 26, 2022 in corresponding PCT/IN2022/050442.

Barnard et al. Evaluation of immunomodulators, interferons and known in vitro SARS-COV inhibitors for inhibition of SARS-CoV replication in BALB/c mice, Antiviral Chemistry & Chemotherapy, vol. 17, pp. 275-284, 2006.

Sheahan et al., An orally bioavailable broad-spectrum antiviral inhibits SARS-CoV-2 in human airway epithelial cell cultures and multiple coronaviruses in mice, Sci. Transl. Med. 12, eabb5883, Apr. 29, 2020, 15 pages.

* cited by examiner

*Primary Examiner* — Layla D Berry
(74) *Attorney, Agent, or Firm* — BLANK ROME LLP

(57) ABSTRACT

This invention provides a process for the preparation of orthogonally protected ribose derivative. Which are further used as donor for the synthesis of N4-hydroxy cytidine and its derivatives by using commercially available materials under very mild reaction condition and short period of time. Thereafter N-hydroxylation of cytidine can be achieved in a short period of time. The intermediates or the final compounds thus obtained can be used for the treatment of viral infections.

12 Claims, 1 Drawing Sheet

PROCESS FOR THE PREPARATION OF N4-HYDROXYCYTIDINE AND ITS DERIVATIVES

CROSS REFERENCE TO RELATED APPLICATIONS

This application claims the benefit of International PCT Application No. PCT/IN2022/050442, filed May 6, 2022, entitled “A Process for the Preparation of N4-Hydroxycytidine and its Derivatives,” which claims priority of India Application No. 202111020678 filed on May 6, 2021, and entitled “Non Infringing Process for the Synthesis of N4-Hydroxycytidine and its Derivatives,” the contents of which are relied upon and incorporated herein by reference in their entirety.

FIELD OF THE INVENTION

Present invention relates to a process for the preparation of N4-hydroxycytidine nucleoside compound of Formula I from ribose.

Formula I

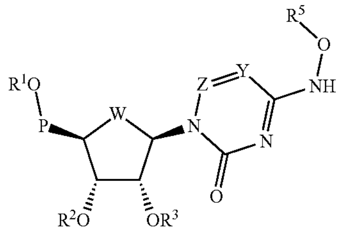

BACKGROUND AND PRIOR ART OF THE INVENTION

3-D-N4-hydroxycytidine (EIDD-1931), an orally bioavailable ribonucleoside derivative, has shown broad-spectrum antiviral activity against diverse unrelated RNA viruses (*Antimicrobial Agents and Chemotherapy.* 2018, 8, 62; *Journal of Virology.* 2018, 3, 92; *Antiviral Chemistry & Chemotherapy.* 2006, 5, 275; *Science Translational Medicine* 2020 12).

EIDD-1931 inhibits replication of acute respiratory syndrome coronavirus (SARS-CoV) in Vero 76 cells, Middle East respiratory syndrome coronavirus (MERS-CoV) in Calu-3 2B4 cells, and SARS-CoV-2 in Vero cells (IC50s=0.1, 0.15 and 0.3 M, correspondingly). (3, 92; *Antiviral Chemistry & Chemotherapy.* 2006, 5, 275; *Science Translational Medicine* 2020 12) Further, there are reports where in it reduces viral titers of Venezuelan equine encephalitis virus (VEEV) TC-83 in infected Vero cells (EC50=0.426 M) and remdesivir-resistant strains of the model CoV mouse hepatitis virus (MHV) in infected DBT cells. (*Journal of Virology.* 2018, 3, 92; *Antiviral Chemistry & Chemotherapy.* 2006, 5, 275; *Science Translational Medicine* 2020 12) Virologists in the lab of Ralph Baric (Prof. William R. Kenan) are working with colleagues in the lab of Mark Denison, Pro. Edward Claiborne Stahlman (Vanderbilt University Medical Center), Prof George Painter (Drug Innovation Ventures at Emory) and director of the Emory Institute for Drug Development (EIDD).

Denison laboratory established that EIDD-1931 blocked the replication of a broad spectrum of coronaviruses. Maria Agostini, a postdoctoral fellow in the Denison lab, demonstrated that the viruses showing resistance to remdesivir experience higher inhibition from EIDD-1931.

Viruses prone to remdesivir resistance mutations are actually more vulnerable to EIDD-1931 and vice versa, signifying that the two drugs could be useful in combination for improved efficacy and to avert the emergence of resistance. In view of the escalating demand for EIDD molecules for the cure of COVID-19, new and more efficient routes to EIDD-1931 are needed. N4-hydroxycytidine and its different analogues have been synthesized and patented before.

The disclosure by Emory University covered in two different patents already presented the N4-hydroxycytidine nucleoside derivatives, compositions, and methods related thereto.

References may be made to patent application WO2016/106050A1, which describes the synthesis of N4-hydroxy cytidine from cytidine, solution of hydroxylamine hydrochloride in water was prepared, and adjusted to pH=6 with a small amount of aq. NaOH. A sealable pressure tube was charged with this solution and cytidine and heated with stirring at 37° C. for 16 h, this procedure takes more time and includes tedious workup procedures and purification procedure by employing reverse phase flash chromatography.

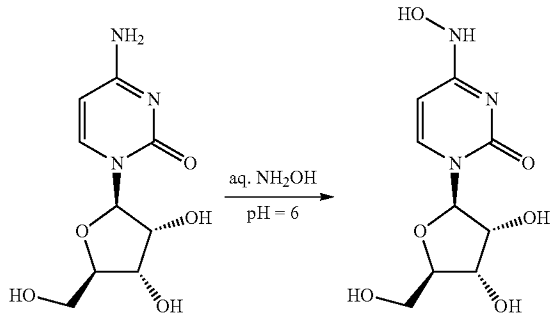

Cytidine EIDD-1931

References may be made to patent application WO2019/113462 A1, which describes the synthesis of N4-hydroxy cytidine from uridine, the compound can be made in one step from cytidine by heating in a pH-adjusted solution of hydroxylamine. Despite being shorter, this route tends to give lower yields and requires tedious workup and purification by reverse phase flash column chromatography, limiting its use to producing smaller quantities.

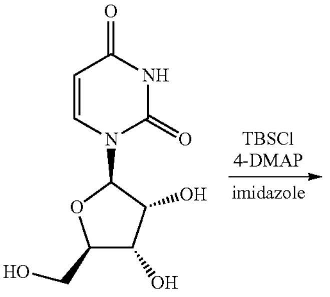

Uridine

-continued

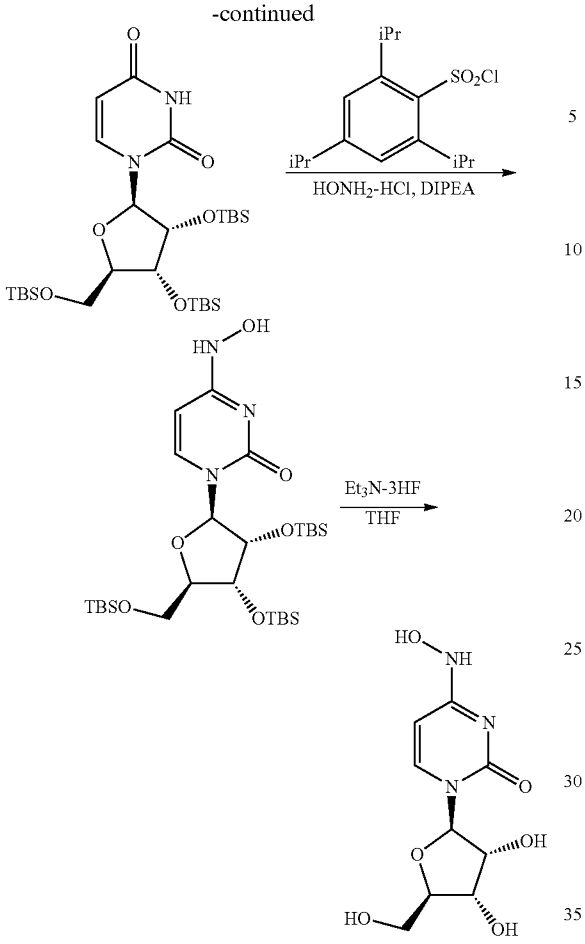

EIDD-1931

References may be made to Journal, Chemical Communication, 2020, 56, 13363, which reported two steps process of EIDD-2801 by the selective acylation and direct amination of cytidine, where starting material used is not available in bulk quantity.

The present invention describes an improved route for the synthesis of 3-D-N4-hydroxycytidine and its analogues starting from ribose involving different intermediate synthesis procedures and coupling conditions. Further, the present invention also established an improvised method for N-hydroxylation of cytidine and its derivatives.

The present invention has various merits over previous methods such as:

i. avoids the use of buffer;

ii. completes the reaction in lesser time (2 hrs);

iii. ease in purification.

The present invention proposes a development of novel process for the synthesis of N4-hydroxycytidine from commercially available starting materials, requires very mild reaction condition and short period of time.

OBJECTIVE OF THE INVENTION

The main objective of present disclosure is to provide an economical process for the synthesis of N4-hydroxycytidine nucleoside compound of Formula I currently under consideration for the treatments of COVID-19 infections.

Another objective of the present invention is to provide simple route for the N-hydroxylation procedure of cytidine and its analogues.

SUMMARY OF THE INVENTION

Figure 1:
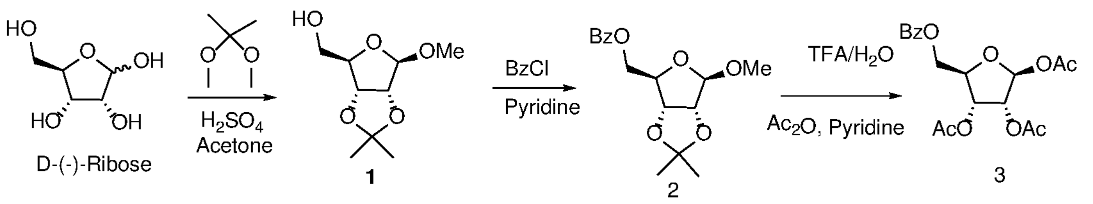
FIG. 1 represents the synthetic approach for preparation of compound of Formula 3.
Figure 2:
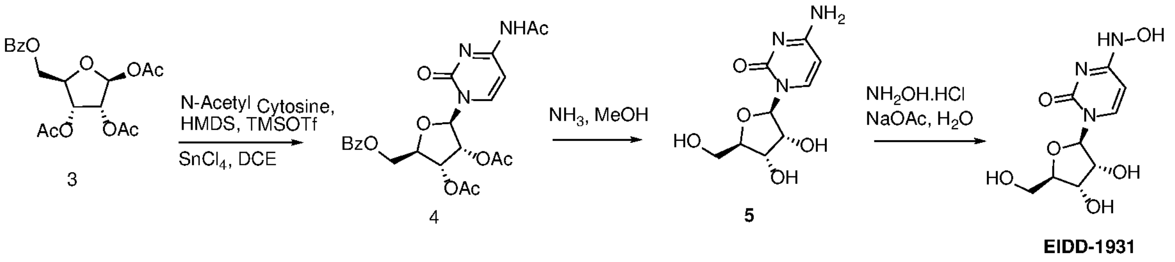
FIG. 2 represents the synthetic approach for preparation of compound of Formula I EIDD-1931.
Figure 3:
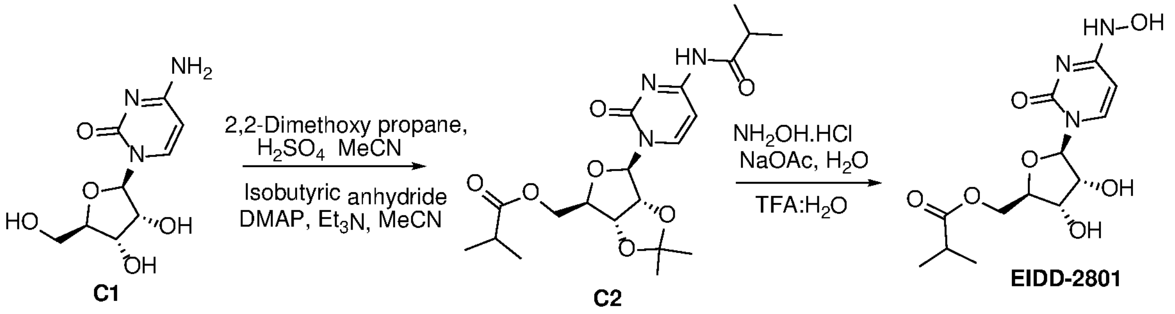
FIG. 3 represents the synthetic approach for preparation of compound of EIDD-2801.

Accordingly, present invention provides a process for the preparation of a compound of Formula Formula I

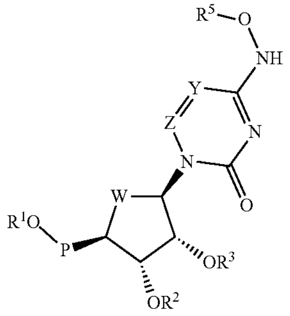

wherein

W is selected from the group consisting of NH, S or O;

P is independently selected from the group consisting of $CH_2$, $CHCH_3$, $C(CH_3)_2$, CHF, $CF_2$, or $CD_2$;

Y is selected from N or CR';

Z is selected from N or CR";

$R^1$, $R^2$, $R^3$, and $R^5$ are each independently selected from the group consisting of H, optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, hammline L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis- (acyloxybenzyl)esters, optionally substituted (acyloxybenzyl)esters, and BAB-esters;

R' and R" are independently selected from the group consisting of hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl;

comprising the steps of:

i. reacting the intermediate compound of Formula 3 with a substituted nucleobase compound in presence of a lewis acid and a solvent to obtain the compound of Formula 4;

Formula 3

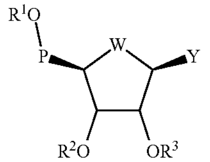

Formula 4

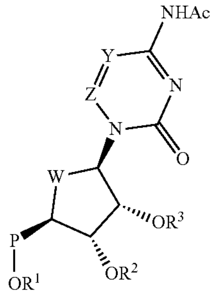

wherein Y' is Cl, OAc, SPh, Br, OH, or OMe, ii. deacetylation of compound of Formula 4 as obtained in step (i) in presence of ammonia and MeOH to obtain compound of Formula 5;

Formula 5

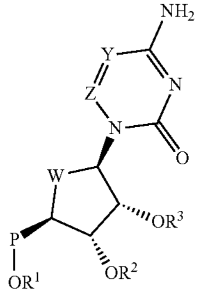

iii. N-hydroxylation of compound of Formula 5 as obtained in step (ii) with $NH_2OH$ HCl and salt in presence of water to obtain compound of Formula I.

Formula I

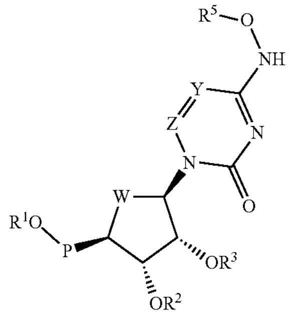

In an embodiment of the present invention, nucleobase is selected from the group comprising of:

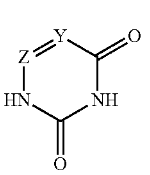

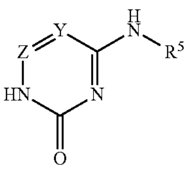

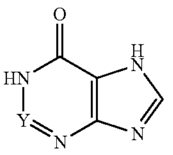

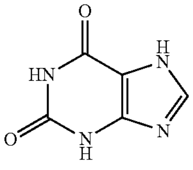

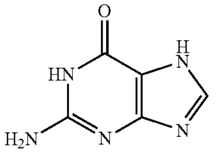

In another embodiment of the present invention, the substituted nucleobase compound is activated in hexamethyldisilazane (HMIDS) in presence of trimethylsilyl trifluoromethanesulfonate (TMSOTf) at 60° C. to 120° C. in solvent under anhydrous conditions.

In yet another embodiment of the present invention, the Lewis acid used is selected from the group consisting of tin tetrachloride, zinc chloride, $BF_3$ etherate, indium chloride, zinc bromide, aluminium chloride.

In yet another embodiment of the present invention, the solvent is selected from the group consisting of dry acetonitrile, dichloroethane or combination thereof.

In yet another embodiment of the present invention, compound of formula I is selected from the group comprising of:

Formula II

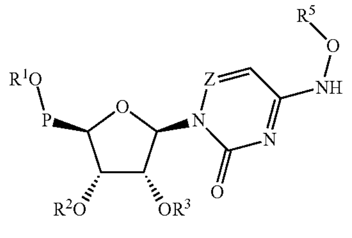

-continued
Formula III
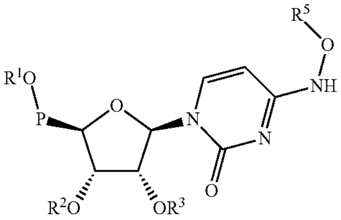
Formula IV
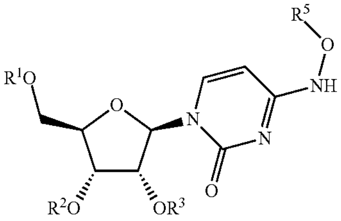
Formula V
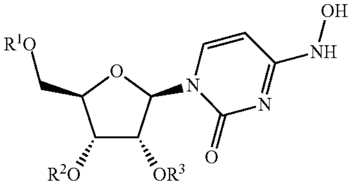
Formula VIa
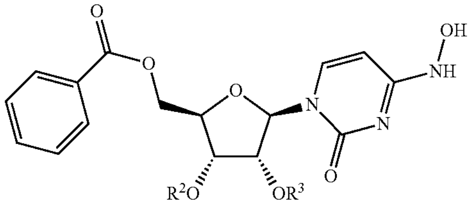
Formula VIb
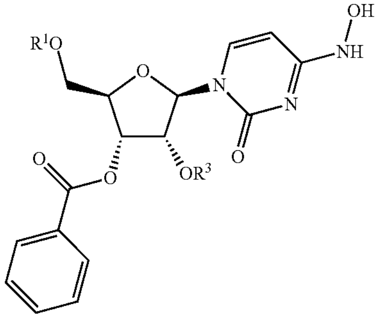
Formula VIc
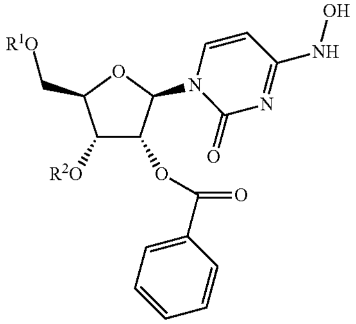
-continued
Formula VId
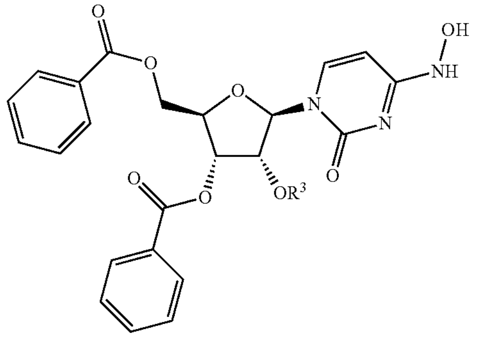
Formula VIe
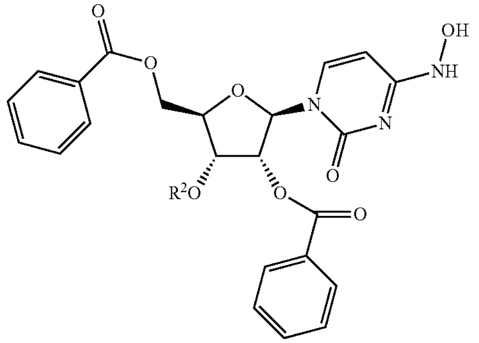
Formula VIf
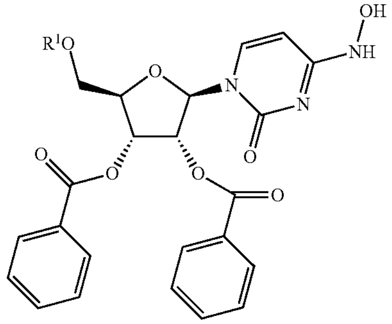
Formula VII
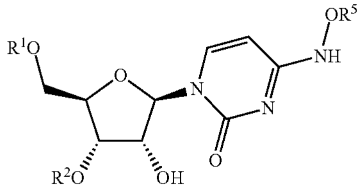
Formula VIII
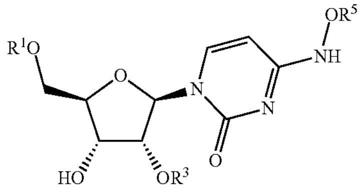

-continued

Formula IX

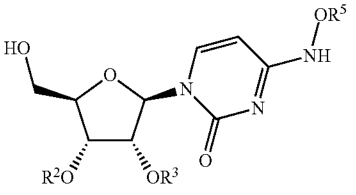

Formula X

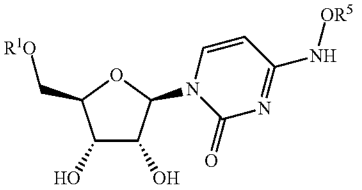

Formula XI

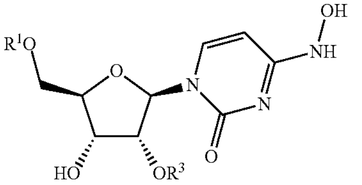

Formula XII

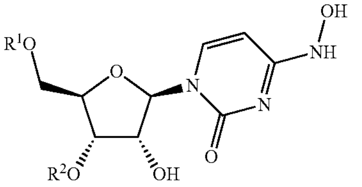

Formula XIII

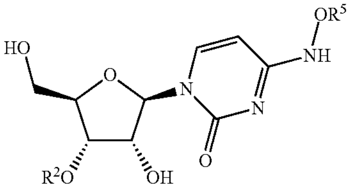

Formula XIV

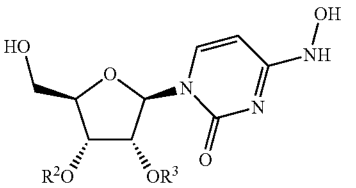

Formula XV

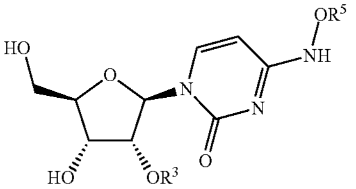

Formula XVI

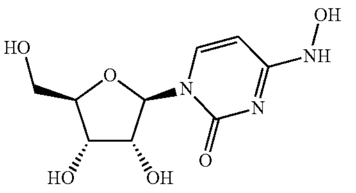

-continued

Formula XVII

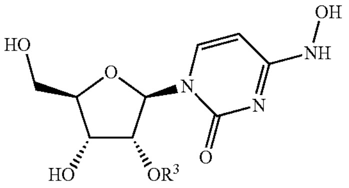

Formula XVIII

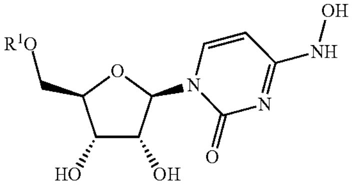

Formula XIX

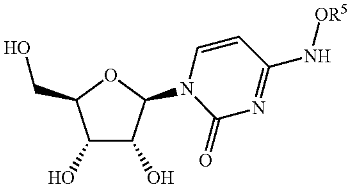

In yet another embodiment, present invention provides a process for the preparation of EIDD-2801

EIDD-2801

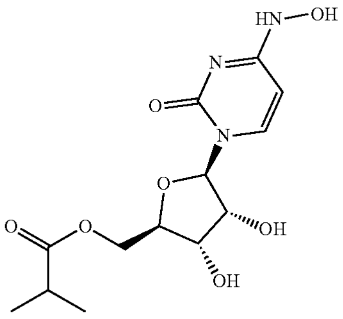

comprising the steps of:

i) acetonide protection of cytidine compound of Formula C1 in presence of acid to obtain acetonide protected cytidine;

C1

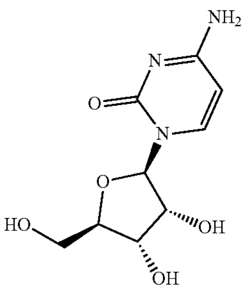

ii) diesterification of acetonide protected cytidine as obtained in step (i) in presence of base to obtain compound of Formula C2;

C2

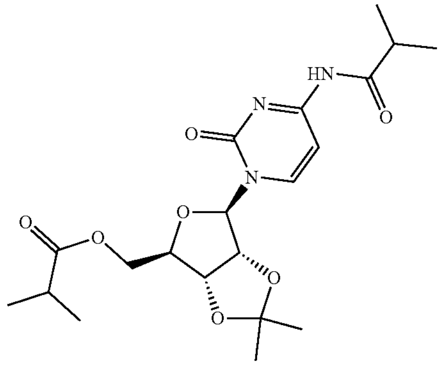

iii) N-hydroxylation of compound of Formula C2 as obtained in step (ii) in presence of salt to obtain N-hydroxylated cytidine;

iv) deprotection of N-hydroxylated cytidine as obtained in step (iii) in presence of deprotecting agent & water to obtain EIDD-2801.

In yet another embodiment of the present invention, the acetonide protecting agent used is selected from 2,2 dimethoxypropane, Acetone or 2-methoxypropane.

In yet another embodiment of the present invention, the reagent used is selected from the group consisting of isobutyric anhydride, isobutyryl chloride, acetic anhydride, benzoic anhydride, benzoyl chloride thereof.

In yet another embodiment of the present invention, the base used is selected from the group consisting of triethylamine, trimethylamine, dimethyl amino pyridine, pyridine, pyrrolidine, imidazole or combination thereof.

In yet another embodiment of the present invention, the reagent used is selected from the group consisting of hydroxylamine hydrochloride, perchloroacetate or combination thereof.

In yet another embodiment of the present invention, the salt used is selected from the group consisting of ammonium acetate, sodium acetate, potassium acetate, potassium carbonate and cesium carbonate or combination thereof.

In yet another embodiment of the present invention, the deprotecting agent used is selected from the group consisting of trifluoroacetic acid, acetic acid, formic acid or para toluene sulphonic acid.

DETAIL DESCRIPTION OF THE INVENTION

Present invention provides a process for preparation of compound of Formula I

Formula I

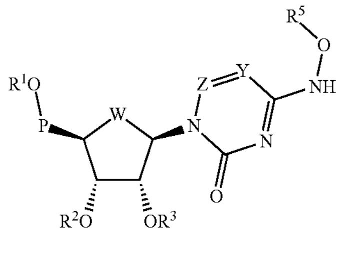

wherein

W is selected from the group consisting of NH, S or O;

P is independently selected from the group consisting of $CH_2$, $CHCH_3$, $C(CH_3)_2$, CHF, $CF_2$, or $CD_2$;

Y is selected from N or CR';

Z is selected from N or CR";

$R^1$, $R^2$, $R^3$, and $R^5$ are each independently selected from the group consisting of H, optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters;

R' and R" are independently selected from the group consisting of hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl;

comprising the steps of.

i. reacting the intermediate compound of Formula 3

Formula 3

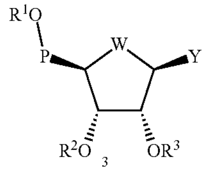

3 wherein Y' is Cl, OAc, SPh, Br, OH, or OMe, with a substituted nucleobase compound in presence of a lewis acid and a solvent to obtain the compound of Formula 4;

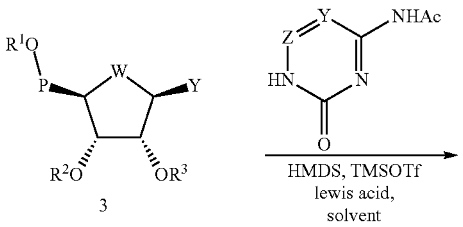

3

-continued

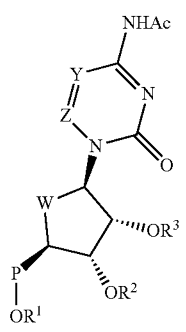

4

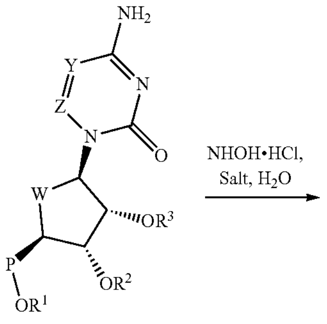

5

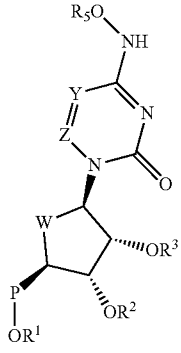

Formula I ii. deacetylation of compound of Formula 4 obtained in step-i in presence of ammonia and MeOH to obtain compound of Formula-5;

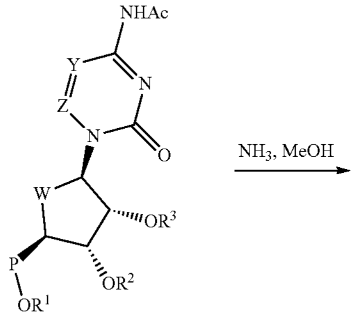

4

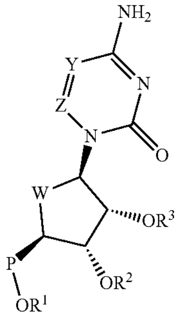

5 iii. N-hydroxylation of compound of Formula-5 obtained in stage-ii with $NH_2OH$ HCl and salt in presence of water to obtain compound of Formula I.

The substituted Nucleobase comprises of

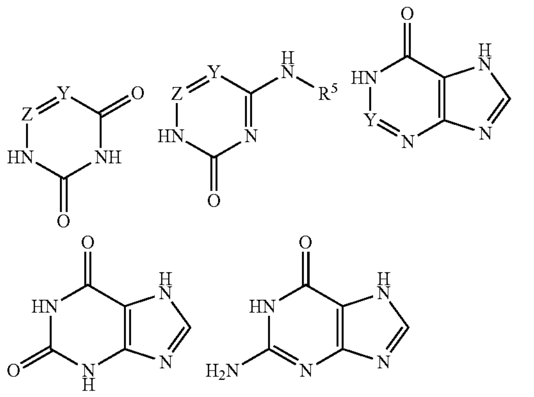

The substituted nucleobase is activated in hexamethyldisilazane (HMDS) in the presence of trimethylsilyl trifluoromethanesulfonate (TMSOTf) at 60° C. to 120° C. in dichloroethane under anhydrous conditions.

Lewis acid is selected from the list of tin tetrachloride, zinc chloride, $BF_3$ etherate, indium chloride, zinc bromide, aluminium chloride or combination thereof.

The solvent is selected from dry acetonitrile, dichloroethane or combination thereof.

As used herein, "alkyl" means a straight or branched chain saturated hydrocarbon moieties such as those containing from 1 to 10 carbon atoms. A "higher alkyl" refers to saturated hydrocarbon having 11 or more carbon atoms. A "C6-C16" refers to an alkyl containing 6 to 16 carbon atoms. Likewise a "C6-C22" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like.

As used herein, the term "alkenyl" refers to unsaturated, straight or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH═CEh; 1-propenyl refers to a group with the structure-CH═CH—$CH_3$; and 2-propenyl refers to a group with the structure —$CH_2$—CH═$CH_2$. Asymmetric structures such as $(Z_1Z_2)$ C═C$(Z_3Z_1)$ are intended to include both the E and Z isomers. This can be presumed in structural formulae herein wherein an asymmetric alkene is present, or it can be explicitly indicated by the bond symbol C═C.

As used herein, the term "alkynyl" represents straight or branched hydrocarbon moieties containing a triple bond. Unless otherwise specified, $C_2$-$C_{24}$ (e.g., $C_2$-$C_{24}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Non-aromatic mono or polycyclic alkyls are referred to herein as "carbocycles" or "carbocyclyl" groups.

Representative saturated carbocycles include cyclopropyl, cyclobutyl, cyclopentyl, cyclohexyl, and the like; while unsaturated carbocycles include cyclopentenyl and cyclohexenyl, and the like. "Heterocarbocycles"or heterocarbocyclyl" groups are carbocycles which contain from 1 to 4 heteroatoms independently selected from nitrogen, oxygen and sulfur which can be saturated or unsaturated (but not aromatic), monocyclic or polycyclic, and wherein the nitrogen and sulfur heteroatoms can be optionally oxidized, and the nitrogen heteroatom can be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems can, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems can be aromatic, non-aromatic or mixtures of aromatic and non-aromatic rings. Heterocycle includes heterocarbocycles, heteroaryls, and the like. "Alkylthio" refers to an alkyl group as defined above with the indicated number of carbon atoms attached through a sulfur bridge.

An example of an alkylthio is methylthio, (i.e., —S—$CH_3$). "Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy.

Preferred alkoxy groups are methoxy, ethoxy, n-propoxy, i-propoxy, n-butoxy, s-butoxy, t-butoxy. "Alkylamino" refers an alkyl group as defined above with the indicated number of carbon atoms attached through an amino bridge.

An example of an alkylamino is methylamino, (i.e., —NH—$CH_3$). "Alkanoyl" refers to an alkyl as defined above with the indicated number of carbon atoms attached through a carbonyl bride (i.e., —(C═O) alkyl). “Alkylsulfonyl” refers to an alkyl as defined above with the indicated number of carbon atoms attached through a sulfonyl bridge (i.e., —S(═O)$_2$alkyl) such as mesyl and the like, and “Arylsulfonyl” refers to an aryl attached through a sulfonyl bridge (i.e., —S(═O)$_2$ aryl). “Alkylsulfamoyl” refers to an alkyl as defined above with the indicated number of carbon atoms attached through a sulfamoyl bridge (i.e., —NHS(═O)$_2$alkyl), and an “Arylsulfamoyl” refers to an alkyl attached through a sulfamoyl bridge (i.e., —NHS(═O)$_2$ aryl). “Alkylsulfmyl” refers to an alkyl as defined above with the indicated number of carbon atoms attached through a sulfmyl bridge (i.e. —S(═O)alkyl). The terms “cycloalkyl” and “cycloalkenyl” refer to mono-, bi-, or tri homocyclic ring groups of 3 to 15 carbon atoms which are, respectively, fully saturated and partially unsaturated.

The term “cycloalkenyl” includes bi- and tricyclic ring systems that are not aromatic as a whole, but contain aromatic portions (e.g., fluorene, tetrahydronapthalene, dihydroindene, and the like). The rings of multi-ring cycloalkyl groups can be either fused, bridged and/or joined through one or more spiro unions. The terms “substituted cycloalkyl” and “substituted cycloalkenyl” refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms “halogen” and “halo” refer to fluorine, chlorine, bromine, and iodine. The term “substituted” refers to a molecule wherein at least one hydrogen atom is replaced with a substituent. When substituted, one or more of the groups are “substituents.” The molecule can be multiply substituted.

In the case of an oxo substituent (“═O”), two hydrogen atoms are replaced. Example substituents within this context can include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context can be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term “optionally substituted” as used herein, means that substitution with an additional group is optional and therefore it is possible for the designated atom to be unsubstituted. Thus, by use of the term “optionally substituted” the disclosure includes examples where the group is substituted and examples where it is not.

Examples of prodrugs that can be used to improve bioavailability include esters, optionally substituted esters, branched esters, optionally substituted branched esters, carbonates, optionally substituted carbonates, carbamates, optionally substituted carbamates, thioesters, optionally substituted thioesters, branched thioesters, optionally substituted branched thioesters, thiocarbonates, optionally substituted thiocarbonates, S-thiocarbonate, optionally substituted S-thiocarbonate, dithiocarbonates, optionally substituted dithiocarbonates, thiocarbamates, optionally substituted thiocarbamates, oxymethoxycarbonyl, optionally substituted oxymethoxycarbonyl, oxymethoxythiocarbonyl, optionally substituted oxymethoxythiocarbonyl, oxymethylcarbonyl, optionally substituted oxymethylcarbonyl, oxymethylthiocarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, sulfenyl, optionally substituted sulfenyl, imidate, optionally substituted imidate, hydrazonate, optionally substituted hydrazonate, oximyl, optionally substituted oximyl, imidinyl, optionally substituted imidinyl, imidyl, optionally substituted imidyl, aminal, optionally substituted aminal, hemiaminal, optionally substituted hemiaminal, acetal, optionally substituted acetal, hemiacetal, optionally substituted hemiacetal, carbonimidate, optionally substituted carbonimidate, thiocarbonimidate, optionally substituted thiocarbonimidate, carbonimidyl, optionally substituted carbonimidyl, carbamimidate, optionally substituted carbamimidate, carbamimidyl, optionally substituted carbamimidyl, thioacetal, optionally substituted thioacetal, S-acyl-2-thioethyl, optionally substituted S-acyl-2-thioethyl, bis-(acyloxybenzyl)esters, optionally substituted bis-(acyloxybenzyl)esters, (acyloxybenzyl) esters, optionally substituted (acyloxybenzyl)esters, and BAB-esters.

EXAMPLES

Following examples are given by way of illustration and therefore should not be construed to limit the scope of the invention.

All chemical reactions were performed in oven-dried glassware under a nitrogen atmosphere, except where noted. Chemicals and solvents were reagent-grade and purchased from commercial suppliers (typically Aldrich, Fisher and TCI) and used as received, excepting where noted. All reactions were followed by thin layer chromatography (TLC) to completion, unless stated otherwise. TLC analysis was performed on silica gel, using illumination with a UV lamp (254 nm) or staining with ceric ammonium sulfate and heating. Purification of compounds was performed with Silica gel 60-120 mesh by column chromatography.

$^1$H NMR spectra were measured on a 400 MHz instrument, and processed using MestReNova software. Chemical shifts were measured relative to the appropriate solvent peak: $CDCl_3$ (δ 7.27), DMSO-$D_6$ (δ 2.50), $CD_3OD$ (δ 3.31), $D_2O$ (δ 4.79).

The following abbreviations were used to describe coupling: s=singlet, d=doublet, t=triplet, q=quartet, p=pentet, m=multiplet, br=broad. $^{13}$C NMR spectra were measured on an instrument at 101 MHz with chemical shifts relative to the appropriate solvent peak: $CDCl_3$ (δ 77.0), DMSO-$D_6$ (δ 39.5), $CD_3OD$ (δ 49.0). High resolution mass spectrometry was performed by LTQ-FTMS using either APCI or ESI.

Example 1

Synthesis of 6-methoxy-2,2-dimethyltetrahydrofuro [3,4-d][1,3]dioxol-4-yl)methanol [1]

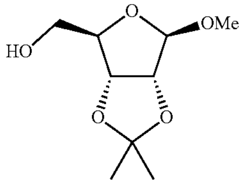

A solution of D(−)Ribose (10 g) in Acetone was charged with 2,2-dimethoxypropane (DMP) (2 equiv) along with catalytic amounts of sulphuric acid and stirred for 16 hours at room temp after complete conversion of starting material, bulk solvent was evaporated under reduced pressure, the reaction mixture was extracted with ethyl acetate and washed with brine, dried over $Na_2SO_4$. The residue was purified by column chromatography to get the desired product as gummy solid. $^1H$ NMR (400 MHz, $CDCl_3$) δ 4.66 (s, 1H), 4.47 (d, J=5.9 Hz, 1H), 4.28 (d, J=5.9 Hz, 1H), 4.03 (d, J=4.3 Hz, 1H), 3.30 (d, J=4.5 Hz, 2H), 3.09 (s, 3H), 1.17 (s, 3H), 1.01 (s, 3H).

Example 2

Synthesis of 6-methoxy-2,2-dimethyltetrahydrofuro [3,4-d][1,3]dioxol-4-yl)methyl benzoate [2]

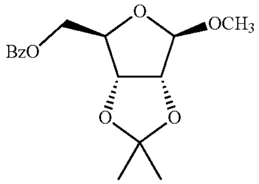

The compound 1 (7 g) was dissolved in pyridine at 0° C. and charged with benzoyl chloride (1.2 equiv.) then stirred for 2 hours at ambient temperature. After completion of the reaction, bulk pyridine was quenched with cupric sulphate solution. The resulting suspension was diluted with $H_2O$ and extracted with ethyl acetate. The combined organic extracts were washed with brine prior to drying over $Na_2SO_4$. The residue was purified by column chromatography to get the desired product as white powder.

$^1H$ NMR (400 MHz, $CDCl_3$) δ 8.01 (d, J=5.6 Hz, 2H), 7.46 (d, J=7.3 Hz, 1H), 7.34 (d, J=9.7 Hz, 2H), 4.95 (s, 1H), 4.69 (d, J=5.9 Hz, 1H), 4.58 (d, J=5.9 Hz, 1H), 4.45 (d, J=6.9 Hz, 1H), 4.28 (dd, J=6.8, 3.7 Hz, 2H), 3.24 (s, 3H), 1.42 (s, 3H), 1.25 (s, 3H).

Example 3

Synthesis of 5-((benzoyloxy)methyl)tetrahydrofuran-2,3,4-triyl triacetate [3]

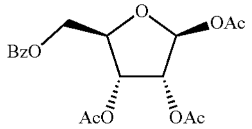

The compound 2 (7 g) was dissolved in a mixture of trifluoroacetic acid and water (9:1) and allowed to stir for 3 hours at room temperature, after complete hydrolysis of starting material bulk solvent was removed under reduced pressure and the crude was diluted with toluene and evaporated multiple times. The hydrolysed product was used as such in next step without purification, where the crude was dissolved in pyridine at −5° C., acetic anhydride (4.5 equiv.) was added and the reaction mixture stirred for 3 hours by allowing the temperature to raise up to room temperature. After complete consumption of starting material, the reaction, mixture was quenched with cupric sulphate solution, diluted with water and extracted with ethyl acetate. The combined extracts were washed with brine, dried with $Na_2SO_4$ and evaporated. The residue was purified by column chromatography (3:1 hexane/EtOAc) to obtain white powder as product.

$^1H$ NMR (400 MHz, $CDCl_3$) δ 7.98 (d, J=7.7 Hz, 2H), 7.49 (t, J=7.3 Hz, 1H), 7.36 (t, J=7.6 Hz, 2H), 6.10 (s, 1H), 5.43 (dd, J=7.0, 5.1 Hz, 1H), 5.31 (d, J=4.7 Hz, 1H), 4.57 (dd, J=12.1, 3.5 Hz, 1H), 4.45-4.39 (m, 1H), 4.30 (dd, J=12.1, 4.4 Hz, 1H), 2.05 (s, 3H), 1.96 (s, 3H), 1.85 (s, 3H).

$^{13}C$ NMR (101 MHz, $CDCl_3$) δ 169.67, 169.39, 168.97, 165.97, 133.31, 129.74, 128.45, 98.26, 79.35, 74.27, 70.53, 63.44, 20.81, 20.47, 20.39.

Example 4

Synthesis of 2-(4-acetamido-2-oxopyrimidin-1(2H)-yl)-5-(acetoxymethyl)tetrahydrofuran-3,4-diyl diacetate

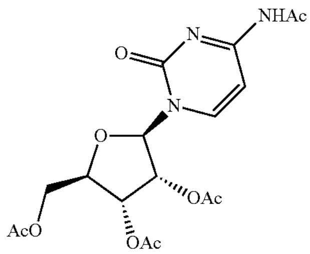

In an atmosphere of nitrogen, N4-acetylcytosine (2.0 equiv.) was dissolved in dichloroethane and hexamethyldisilazae (1.5 equiv.), trifluoromethane sulfonic anhydride (0.1 equiv.) were sequentially added and allowed the reaction mixture to stir at 80° C. for 1 hour, after becoming the reaction mixture translucent the temperature was brought down to 60° C. then Ribose tetraacetate (1.0 equiv.) with stoichiometric amount of tin chloride were added. The reaction was stirred at 60° C. for further 2 hours and extracted with ethyl acetate. The combined extracts were washed with brine, dried over $Na_2SO_4$ and evaporated. The residue was purified by column chromatography (1:1 hexane/EtOAc) to obtain the product.

$^1$H NMR (400 MHz, $CDCl_3$) δ 10.10 (s, 1H), 7.81 (d, J=7.6 Hz, 1H), 7.36 (d, J=7.5 Hz, 1H), 5.94 (d, J=3.6 Hz, 1H), 5.37-5.32 (m, 1H), 5.20 (t, J=5.5 Hz, 1H), 4.28 (d, J=10.8 Hz, 3H), 2.14 (s, 3H), 2.01 (s, 3H), 1.97 (s, 3H), 1.95 (s, 3H). $^{13}$C NMR (101 MHz, $CDCl_3$) δ 171.34, 170.26, 169.55, 169.44, 163.33, 154.98, 144.07, 97.36, 89.43, 79.82, 73.74, 69.65, 62.69, 24.83, 20.75, 20.41.

Example 5

Synthesis of 2-((benzoyloxy)methyl)-5-(2,4-dioxo-3,4-dihydropyrimidin-1(2H)-yl)tetrahydrofuran-3,4-diyl diacetate

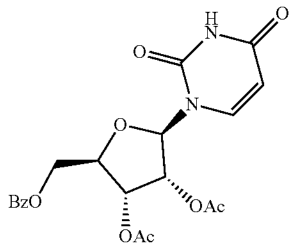

In an atmosphere of nitrogen, uracil (2.0 equiv.) was dissolved in dichloroethane and hexamethyldisilazae (1.5 equiv.), trifluoromethane sulfonic anhydride (0.1 equiv.) were sequentially added and allowed the reaction mixture to stir at 70° C. for 1 hour, after becoming the reaction mixture translucent the temperature was brought down to 60° C. then benzoylated ribose triacetate (1.0 equiv.) with stoichiometric amount of tin chloride were added. The reaction was stirred at 60° C. for further 2 hours and extracted with ethyl acetate. The organic layer were washed with brine, dried over $Na_2SO_4$ and evaporated. The residue was purified by column chromatography (2:1 hexane/EtOAc) to obtain the product.

$^1$H NMR (400 MHz, $CDCl_3$) δ 9.24 (s, 1H), 7.96 (d, J=7.8 Hz, 2H), 7.52 (t, J=7.4 Hz, 1H), 7.39 (t, J=7.8 Hz, 2H), 7.24 (d, J=8.2 Hz, 1H), 5.98 (d, J=5.3 Hz, 1H), 5.48 (d, J=8.1 Hz, 1H), 5.42-5.39 (m, 1H), 5.36 (t, J=5.6 Hz, 1H), 4.64-4.59 (m, 1H), 4.45 (dd, J=12.4, 3.9 Hz, 1H), 4.40-4.36 (m, 1H), 2.04 (s, 3H), 2.02 (s, 3H). $^{13}$C NMR (101 MHz, $CDCl_3$) δ 169.63, 166.00, 162.89, 150.22, 139.30, 133.68, 129.60, 129.21, 128.76, 103.32, 87.55, 80.05, 72.89, 70.32, 63.41, 20.43, 20.34.

Example 6

Synthesis of 2-(4-acetamido-2-oxopyrimidin-1(2H)-yl)-5-((benzoyloxy)methyl) tetrahydrofuran-3,4-diyl diacetate [4]

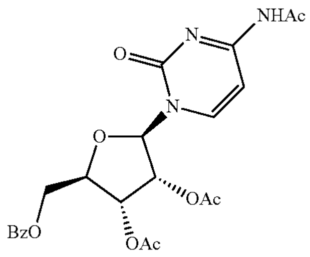

In an atmosphere of nitrogen, N-acetyl cytosine (2.0 equiv.) was dissolved in dichloroethane and hexamethyldisilazae (1.5 equiv.), trifluoromethane sulfonic anhydride (0.1 equiv.) were sequentially added and allowed the reaction mixture to stir at 70° C. for 1 hour, after becoming the reaction mixture translucent the temperature was brought down to 60° C. then benzoylated ribose triacetate (1.0 equiv.) with stoichiometric amount of tin chloride were added. The reaction was stirred at 60° C. for further 2 hours and extracted with ethyl acetate. The organic layer were washed with brine, dried over $Na_2SO_4$ and evaporated. The residue was purified by column chromatography (1:1 hexane/EtOAc) to obtain the product.

$^1$H NMR (400 MHz, $CDCl_3$) δ 8.02 (d, J=7.6 Hz, 2H), 7.91 (d, J=7.6 Hz, 1H), 7.57 (d, J=7.3 Hz, 1H), 7.45 (t, J=7.7 Hz, 2H), 7.31 (d, J=7.6 Hz, 1H), 6.07 (d, J=3.5 Hz, 1H), 5.59-5.53 (m, 1H), 5.45 (t, J=5.9 Hz, 1H), 4.69 (dd, J=12.4, 2.3 Hz, 1H), 4.60-4.50 (m, 2H), 2.22 (s, 3H), 2.06 (s, 3H), 2.04 (s, 3H).

$^{13}$C NMR (101 MHz, $CDCl_3$) δ 170.87, 169.53, 169.44, 166.06, 163.09, 154.97, 144.01, 133.73, 129.62, 129.17, 128.77, 97.33, 89.50, 79.87, 73.86, 69.69, 62.98, 24.82, 20.40.

Example 7

Synthesis of 4-amino-1-[3,4-dihydroxy-5-(hydroxymethyl)tetrahydrofuran-2-yl)pyrimidin-2(1H)-one [5]

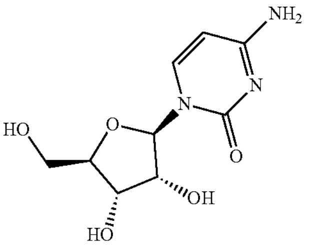 [SMILES: Nc1ccn([C@@H]2O[C@H](CO)[C@@H](O)[C@H]2O)c(=O)n1]

2-(4-acetamido-2-oxopyridin-1(2H)-yl)-5-((benzoyloxy) methyl)tetrahydrofuran-3,4-diyl diacetate (200 mg) was dissolved in 20% of ammonia in methanol solution (3 mL) and allowed to stir at room temperature for 12 hours, after complete deacetylation the solvent was removed under reduced pressure. The product was characterized without purification.

$^1$H NMR (400 MHz, $D_2O$) δ 7.68 (d, J=7.4 Hz, 1H), 5.89 (d, J=7.4 Hz, 1H), 5.73 (s, 1H), 4.14 (d, J=3.9 Hz, 1H), 4.08-4.03 (m, 1H), 3.97 (s, 1H), 3.77 (d, J=12.7 Hz, 1H), 3.65 (dd, J=12.7, 4.2 Hz, 1H).

Example 8

Synthesis of 1-(3,4-dihydroxy-5-(hydroxymethyl) tetrahydrofuran-2-yl)-4-(hydroxyamino)pyrimidin-2 (1H)-one [EIDD-1931]

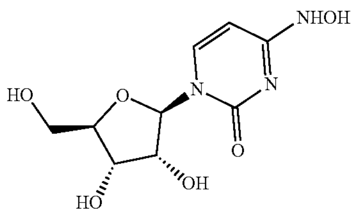

4-amino-1-[3,4-dihydroxy-5-(hydroxymethyl)tetrahydrofuran-2-yl)pyrimidin-2(1H)-one (200 mg) was dissolved in 3 mL of water and hydroxylamine.hydrochloride (4.5 equiv.), sodium acetate (2.5 equiv.) were added, the reaction mixture were allowed to stir at 100° C. for 2 hours until the initial compounds dissolved. The mixture was then slowly evaporated until crystallization began. The precipitate was filtered off and recrystallized from water to obtain the target product as white solid.

1H NMR (400 MHz, DMSO) δ 7.09 (d, J=8.1 Hz, 1H), 5.76 (d, J=5.8 Hz, 1H), 5.61 (d, J=8.1 Hz, 1H), 4.05-3.98 (m, 2H), 3.82 (s, 1H), 3.56 (s, 2H). $^{13}$C NMR (101 MHz, DMSO) δ 150.12, 143.93, 130.67, 98.94, 87.40, 85.04, 72.90, 70.73, 61.76.

Example 9

Synthesis of ((3aR,4R,6R,6aR)-6-(4-isobutyramido-2-oxopyrimidin-1(2H)-yl)-2,2 dimethyltetrahydrofuro[3,4-d][1,3]dioxol-4-yl)methyl isobutyrate (C2)

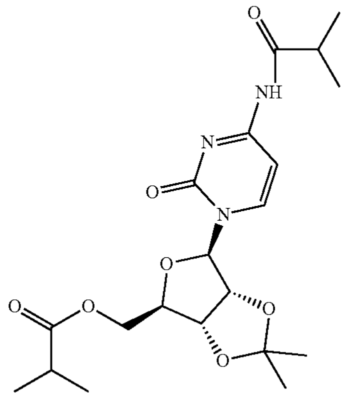 [SMILES: CC(C)C(=O)Nc1ccn([C@@H]2O[C@H](COC(=O)C(C)C)[C@H]3OC(C)(C)O[C@H]32)c(=O)n1]

Cytidine was dissolved in anhydrous acetonitrile in an oven dried 100 mL 3-necked round bottom flask equipped with a Dean-Stark apparatus flushed with nitrogen. 2,2 Dimethoxypropane and 98% $H_2SO_4$ were successively added to it. The reaction mixture was stirred at room temperature for half an hour of time. Then, 10 mL of anhydrous acetonitrile were added and 10 mL of solvent were distilled off. This distillation was performed thrice. After cooling to room temperature, the excess solvent was evaporated under reduced pressure to obtain acetonide protected cytidine. Which was dissolved in acetonitrile (25 mL) in an oven dried round bottom flask, Isobutyric anhydride, triethylamine and 4-Dimethylaminopyridine were added successively. The reaction mixture was stirred at room temperature for 2 h. After completion of reaction, methanol (5 mL) was added to it and continued the stirring for another additional hour.

The solvent was removed under reduced pressure. After addition of 100 mL ethyl acetate, the organic phase was washed with sat. $NaHCO_3$ (2×90 mL), water (50 mL) and brine (50 mL) and dried with $Na_2SO_4$. After removal of the solvent under reduced pressure, the residue was purified by column chromatography by using ethyl acetate and hexane to obtain compound 9 as a whitish solid.

$^1$H NMR (400 MHz, $CDCl_3$) δ 7.81 (d, J=7.5 Hz, 1H), 7.50 (d, J=7.5 Hz, 1H), 5.73 (s, 1H), 5.04 (d, J=6.4 Hz, 1H), 4.85 (dd, J=6.2, 3.9 Hz, 1H), 4.52-4.43 (m, 1H), 4.39-4.30 (m, 2H), 2.77 (dt, J=13.7, 6.8 Hz, 1H), 2.56-2.47 (m, 1H), 1.57 (s, 3H), 1.35 (s, 3H), 1.22 (d, J=1.1 Hz, 3H), 1.20 (d, J=1.2 Hz, 3H), 1.16 (s, 3H), 1.14 (s, 3H). $^{13}$C NMR (101 MHz, $CDCl_3$) δ 177.9, 176.5, 163.6, 154.6, 146.4, 114.1, 96.6, 96.5, 86.3, 85.2, 81.3, 64.2, 36.4, 33.8, 27.1, 25.2, 19.0, 18.9, 18.9, 18.9.

Example 10

Synthesis of ((2R,3S,4R,5R)-3,4-dihydroxy-5-(4-(hydroxyamino)-2-oxopyrimidin-1(2H)-yl)tetrahydrofuran-2-yl)methyl isobutyrate (EIDD 2801)

EIDD-2801

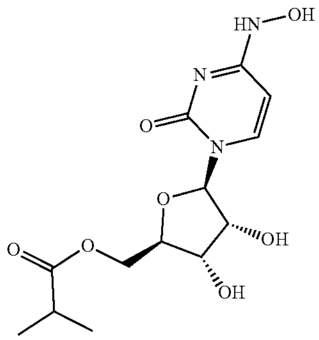

A mixture of compound 9, hydroxylamine hydrochloride and sodium acetate in 50 ml of water was heated at 100° C. for 40 minutes of time. On completely conversion of the starting material, the reaction mixture was cooled to room temperature and extracted with ethyl acetate (2×50 mL). After removal of the solvent under reduced pressure, the residue was purified by column chromatography by using ethyl acetate and hexane which was dissolved in mixture of TFA and water. The reaction mixture was stirred at room temperature for one hour. Excess of TFA was quenched with aqueous solution $NaHCO_3$. The reaction mixture was diluted with water and extracted with ethyl acetate and washed with brine, dried over $Na_2SO_4$. The residue was purified by column chromatography by using dichloromethane and methanol to obtain compound 10 as a whitish gummy solid.

$^1$H NMR (400 MHz, MeOD) δ 6.94 (d, J=8.2 Hz, 1H), 5.72 (d, J=4.7 Hz, 1H), 5.56 (d, J=8.2 Hz, 1H), 4.20 (d, J=3.9 Hz, 2H), 4.06-3.93 (m, 3H), 2.52 (dt, J=14.0, 7.0 Hz, 1H), 1.09 (s, 3H), 1.07 (s, 3H).

$^{13}$C NMR (101 MHz, $CDCl_3$) δ 181.2, 153.4, 149.9, 135.7, 101.5, 93.8, 85.1, 77.5, 73.7, 67.6, 37.9, 22.6, 22.6.

Advantages of the Invention

The present invention deals with novel process of preparation of orthogonally protected ribose derivative.

The present invention deals with novel process of preparation of N4-hydroxy cytidine derivative.

The invention leads to the discovery of novel potent COVID-19 activity synthesized from commercially and economically available starting materials.

The present invention opens up a new avenue for the synthesis of any nucleoside from commercially available ribose and nucleobases.

We claim:

1. A process for the preparation of a compound of Formula I

Formula I

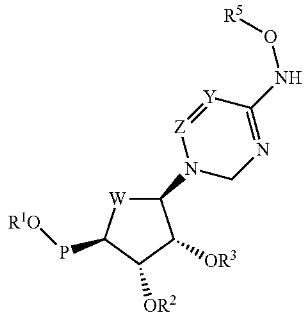

wherein

W is NH, S or O;

P is $CH_2$, $CHCH_3$, $C(CH_3)_2$, CHF, $CF_2$, or $CD_2$;

Y is N or CR';

Z is N or CR";

$R^1$, $R^2$, $R^3$, and $R^5$ are each independently selected from the group consisting of H, optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl) esters, optionally substituted (acyloxybenzyl)esters, and BAB-esters; and R' and R" are each independently selected from the group consisting of hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl;

the process comprising:

i. reacting an intermediate compound of Formula 3 with a substituted nucleobase compound in presence of a lewis acid and a solvent to obtain a compound of Formula 4;

Formula 3

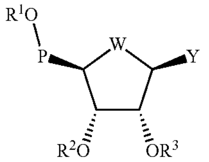

3

Formula 4

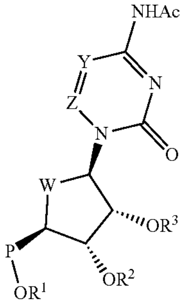

wherein Y' is Cl, OAc, SPh, Br, OH, or OMe;

ii. deacetylation of the compound of Formula 4 in presence of ammonia and MeOH to obtain a compound of Formula 5; and Formula 5

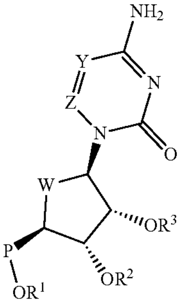

iii. N-hydroxylation of the compound of Formula 5 with $NH_2OH \cdot HCl$ and a salt in the presence of water to obtain the compound of Formula I Formula I

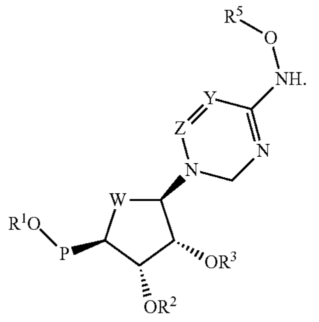

2. The process as claimed in claim 1, wherein the substituted nucleobase compound is activated in hexamethyldisilazane (HMDS) in presence of trimethylsilyl trifluoromethanesulfonate (TMSOTf) at a temperature ranging from 60° C. to 120° C. in a solvent under anhydrous conditions.

3. The process as claimed in claim 1, wherein the Lewis acid used is selected from the group consisting of tin tetrachloride, zinc chloride, $BF_3$ etherate, indium chloride, zinc bromide, and aluminium chloride.

4. The process as claimed in claim 1, wherein the solvent is selected from the group consisting of dry acetonitrile, dichloroethane, and combinations thereof.

5. The process as claimed in claim 1, wherein compound of formula I is selected from the group consisting of:

Formula II

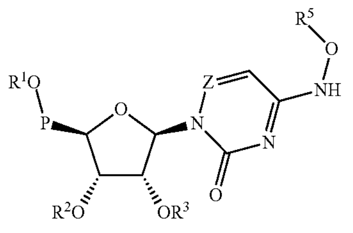

Formula III

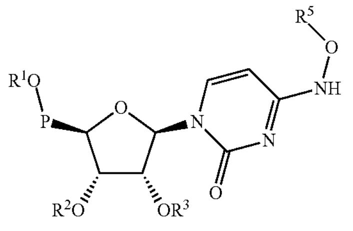

Formula IV

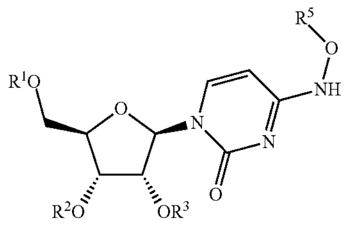

-continued

Formula V

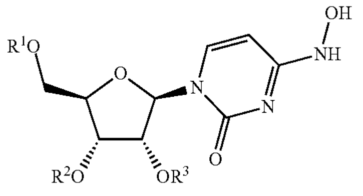

Formula VIa

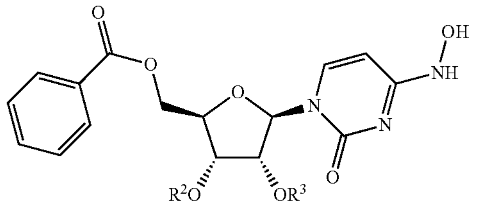

Formula VIb

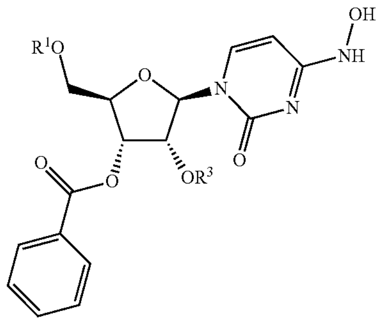

Formula VIc

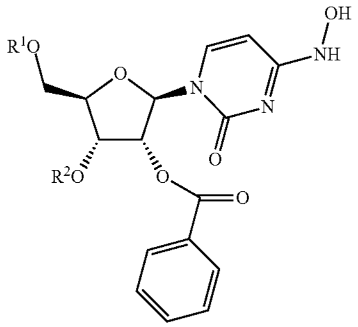

Formula VId

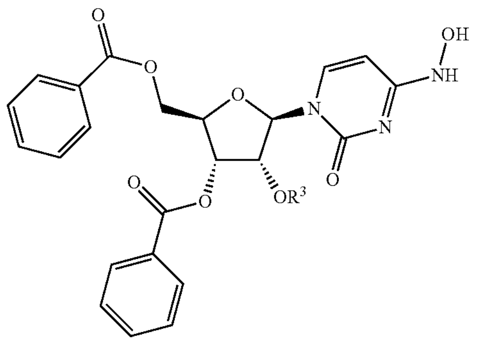

-continued
Formula VIe
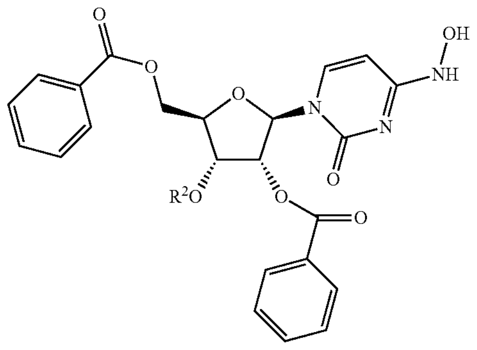
Formula VIf
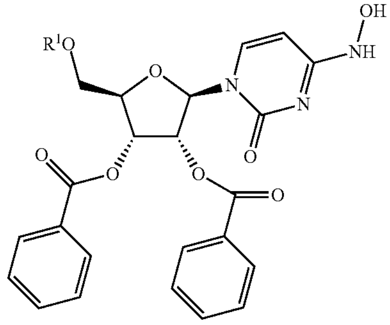
Formula VII
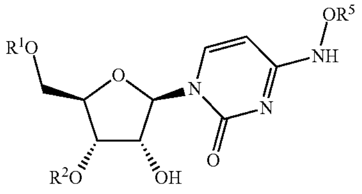
Formula VIII
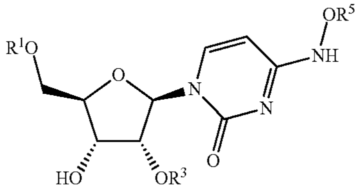
Formula IX
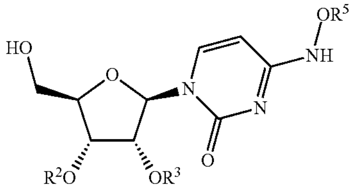
Formula X
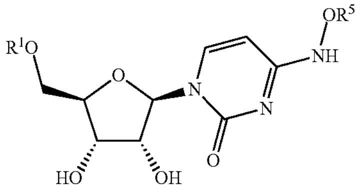
-continued
Formula XI
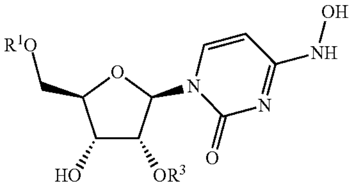
Formula XII
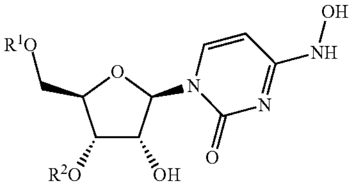
Formula XIII
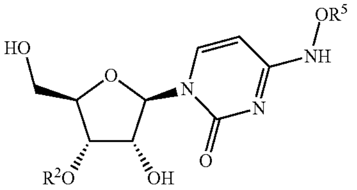
Formula XIV
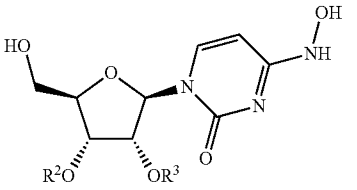
Formula XV
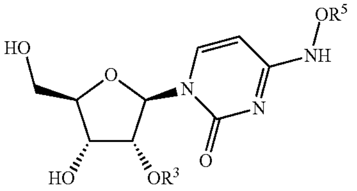
Formula XVI
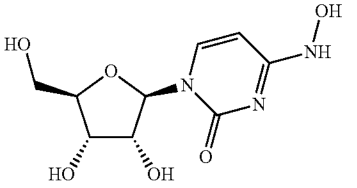
Formula XVII
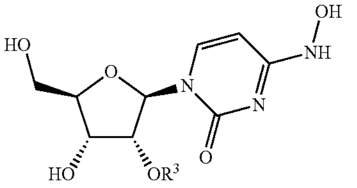
Formula XVIII
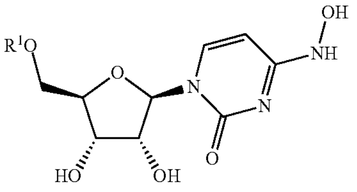

-continued

Formula XIX

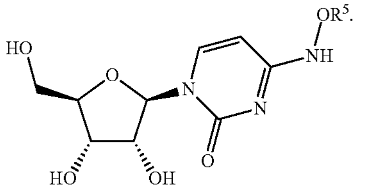

6. A process for the preparation of EIDD-2801

EIDD-2801

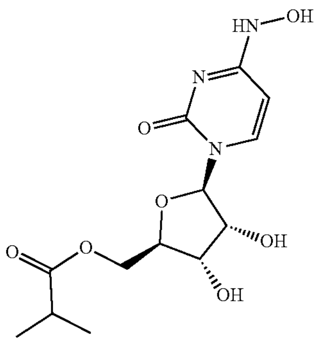

the process comprising:

i) acetonide protection of a cytidine compound of Formula C1 in the presence of an acid to obtain an acetonide-protected cytidine;

C1

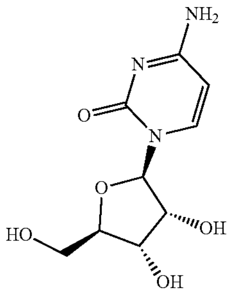

ii) diesterification of the acetonide-protected cytidine in the presence of a base to obtain a compound of Formula C2;

C2

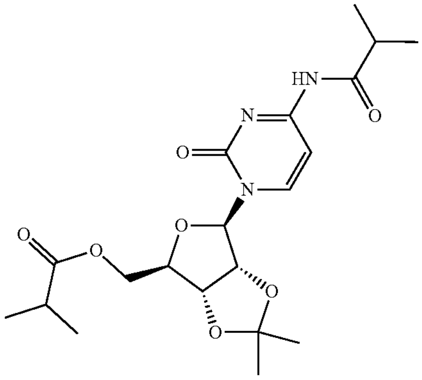

iii) N-hydroxylation of compound of the Formula C2 in the presence of a salt to obtain N-hydroxylated cytidine;

iv) deprotection of the N-hydroxylated cytidine in the presence of a deprotecting agent to obtain EIDD-2801.

7. The process as claimed in claim 6, wherein the acetonide protecting agent used is 2,2 dimethoxypropane, acetone, or 2-methoxypropane.

8. The process as claimed in claim 6, wherein diesterification is performed using a reagent selected from the group consisting of isobutyric anhydride, isobutyryl chloride, acetic anhydride, benzoic anhydride, benzoyl chloride, and any combination thereof.

9. The process as claimed in claim 6, wherein the base is selected from the group consisting of triethylamine, trimethylamine, dimethyl amino pyridine, pyridine, pyrrolidine, imidazole, and any combination thereof.

10. The process as claimed in claim 6, wherein the N-hydroxylation is performed using a reagent selected from the group consisting of hydroxylamine hydrochloride, perchloroacetate, and any combination thereof.

11. The process as claimed in claim 6, wherein the salt is selected from the group consisting of ammonium acetate, sodium acetate, potassium acetate, potassium carbonate, cesium carbonate, and any or combination thereof.

12. The process as claimed in claim 6, wherein the deprotecting agent used is selected from the group consisting of trifluoroacetic acid, acetic acid, formic acid, and para-toluene sulphonic acid.

* * * * *